United States Patent
Mohajer-Shojaee

(10) Patent No.: US 9,579,472 B2
(45) Date of Patent: Feb. 28, 2017

(54) VERESS NEEDLE WITH ILLUMINATED GUIDANCE AND SUTURING CAPABILITY

(71) Applicant: Reza Mohajer-Shojaee, Encino, CA (US)

(72) Inventor: Reza Mohajer-Shojaee, Encino, CA (US)

( * ) Notice: Subject to any disclaimer, the term of this patent is extended or adjusted under 35 U.S.C. 154(b) by 189 days.

(21) Appl. No.: 14/263,291

(22) Filed: Apr. 28, 2014

(65) Prior Publication Data
US 2014/0235954 A1 Aug. 21, 2014

Related U.S. Application Data

(63) Continuation of application No. 13/965,640, filed on Aug. 13, 2013, now abandoned, which is a (Continued)

(51) Int. Cl.
| | |
|---|---|
| *A61B 17/34* | (2006.01) |
| *A61M 13/00* | (2006.01) |
| *A61B 17/04* | (2006.01) |
| *A61B 1/06* | (2006.01) |
| *A61B 17/29* | (2006.01) |
| *A61B 17/295* | (2006.01) |
| *A61B 17/00* | (2006.01) |

(52) U.S. Cl.
CPC ............ *A61M 13/003* (2013.01); *A61B 1/06* (2013.01); *A61B 17/0469* (2013.01); *A61B 17/3474* (2013.01); *A61B 17/0483* (2013.01); *A61B 17/29* (2013.01); *A61B 17/295* (2013.01); *A61B 17/3496* (2013.01); *A61B 2017/00349* (2013.01); *A61B 2017/00353* (2013.01); *A61B 2017/00663* (2013.01); *A61B 2017/00907* (2013.01); *A61B 2090/309* (2016.02)

(58) Field of Classification Search
CPC ...... A61B 17/3474; A61B 2017/00349; A61B 17/0469; A61B 1/06; A61M 13/003
See application file for complete search history.

(56) References Cited

U.S. PATENT DOCUMENTS

| | | |
|---|---|---|
| 589,911 A | 9/1897 | Smith |
| 4,808,168 A | 2/1989 | Warring |

(Continued)

*Primary Examiner* — Aarti B Berdichevsky
(74) *Attorney, Agent, or Firm* — Michael J. Berchou, Esq.; Timothy W. Menasco, Esq.; Harter Secrest & Emery LLP

(57) ABSTRACT

A laparoscopic instrument for forming an incision in a body cavity, insufflating the body cavity with gas, and suturing the incision at the completion of the surgery includes a set of jaws at the distal end of the Veress needle or cannula. The jaws are pivoted to one another for motion between an open position or a closed position in which they may be used to grasp a suture in the body cavity for removal from the cavity for knotting. A push mechanism at the proximal end of the instrument moves the jaws between their open and closed position on successive actuations of a pushbutton and retains them in that state until the next push. An illumination source is provided for the distal end of the instrument to provide illumination through the walls of the body cavity so that the surgeon can determine the degree of penetration of the instrument into the body cavity and can identify any major arteries which should be avoided in the formation of other laparoscopic openings.

7 Claims, 8 Drawing Sheets

Related U.S. Application Data continuation-in-part of application No. 12/693,079, filed on Jan. 25, 2010, now Pat. No. 8,523,817.

(60) Provisional application No. 61/146,974, filed on Jan. 23, 2009.

(56) References Cited

U.S. PATENT DOCUMENTS

| | | |
|---|---|---|
| 4,991,998 A | 2/1991 | Kamino et al. |
| 5,098,388 A | 3/1992 | Kulkashi et al. |
| 5,125,553 A | 6/1992 | Oddsen et al. |
| 5,220,928 A | 6/1993 | Oddsen et al. |
| 5,364,365 A | 11/1994 | Wortrich |
| 5,364,410 A | 11/1994 | Failla et al. |
| 5,374,252 A | 12/1994 | Banks et al. |
| 5,415,666 A | 5/1995 | Gourlay et al. |
| 5,569,292 A | 10/1996 | Scwemberger et al. |
| 5,591,192 A | 1/1997 | Privitera et al. |
| 5,607,435 A * | 3/1997 | Sachdeva ............ A61B 1/0058 359/819 |
| 5,618,291 A | 4/1997 | Thompson et al. |
| 5,632,717 A | 5/1997 | Yoon |
| 5,685,856 A | 11/1997 | Lehrer |
| 5,899,911 A | 5/1999 | Carter |
| 5,964,773 A | 10/1999 | Greenstein |
| 6,309,397 B1 | 10/2001 | Julian et al. |
| 6,387,043 B1 | 5/2002 | Yoon |
| 6,494,893 B2 | 12/2002 | Dubrul et al. |
| 6,669,708 B1 * | 12/2003 | Nissenbaum ........... A61B 17/11 604/164.04 |
| 6,800,076 B2 * | 10/2004 | Humayun ............. A61M 1/008 128/898 |
| 6,984,237 B2 | 1/2006 | Hatch et al. |
| 8,523,817 B2 * | 9/2013 | Mohajer ............ A61B 17/3474 604/158 |
| 8,838,206 B2 * | 9/2014 | Mohajer ............ A61B 17/3474 600/424 |
| 2002/0042620 A1 | 4/2002 | Julian et al. |
| 2006/0268570 A1 | 11/2006 | Vayser et al. |
| 2007/0179455 A1 | 8/2007 | Geliebter et al. |
| 2007/0270653 A1 | 11/2007 | Vayser et al. |
| 2009/0105752 A1 * | 4/2009 | Shonteff ........... A61B 17/06066 606/223 |
| 2010/0081988 A1 * | 4/2010 | Kahle ................ A61B 17/3417 604/26 |
| 2011/0288582 A1 * | 11/2011 | Meade ............... A61B 17/0469 606/226 |

\* cited by examiner

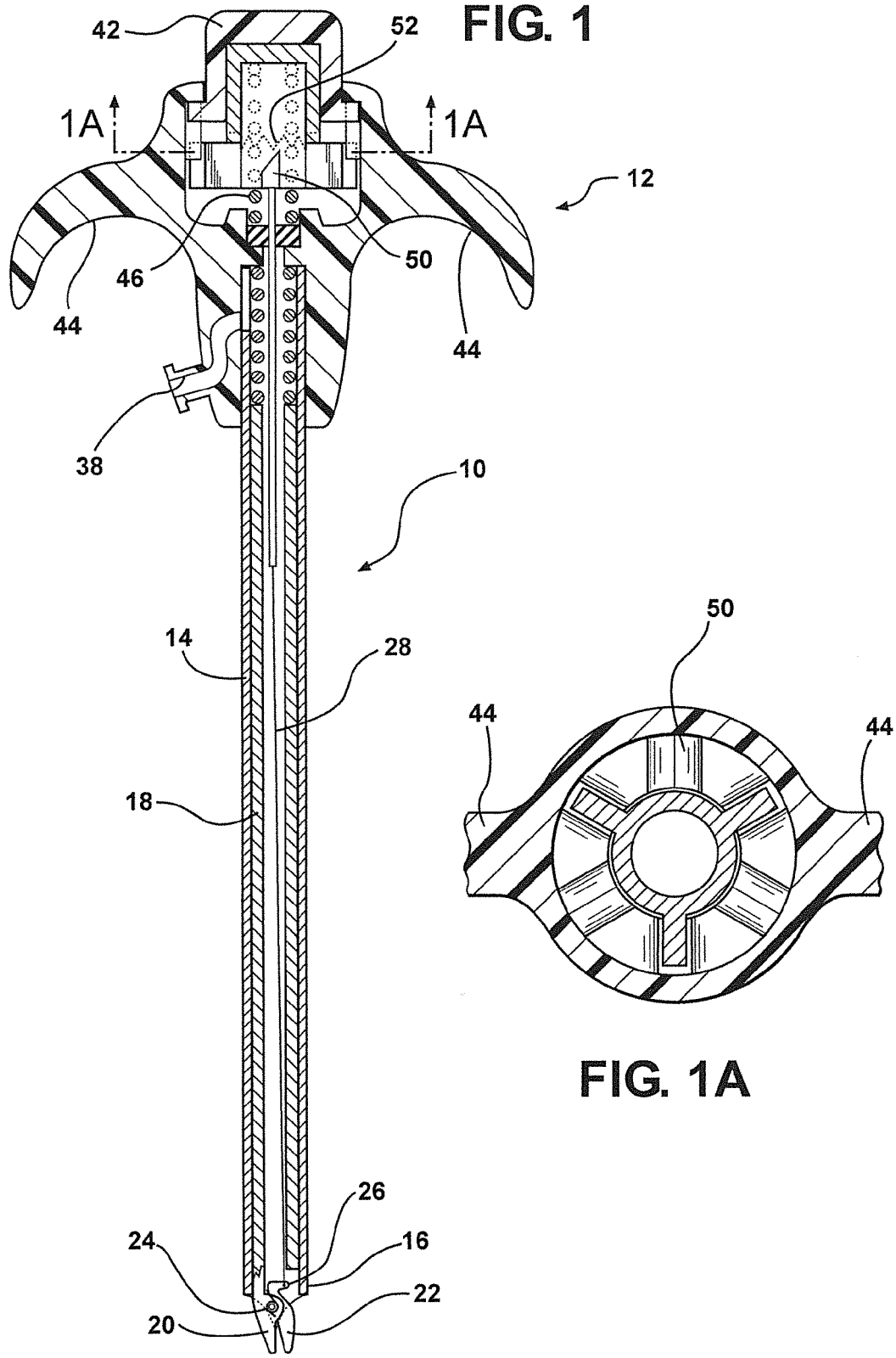

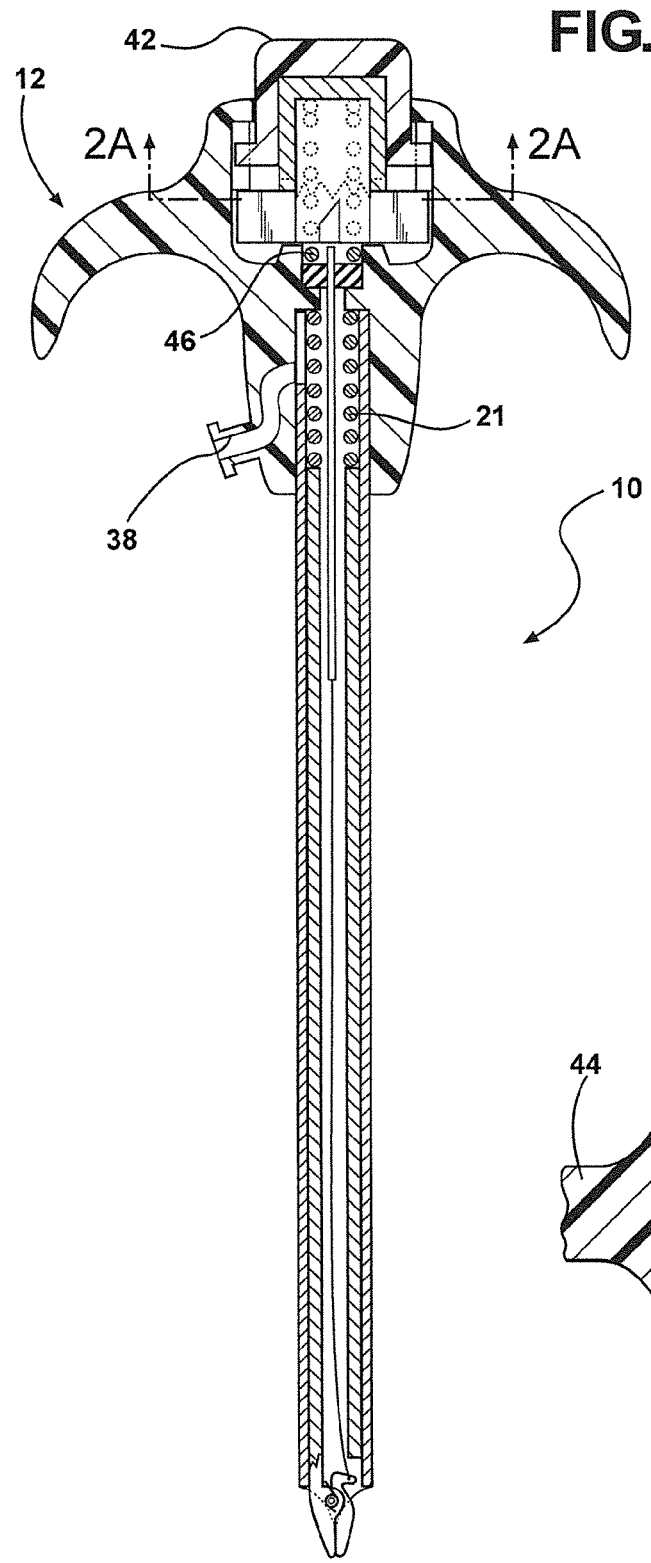
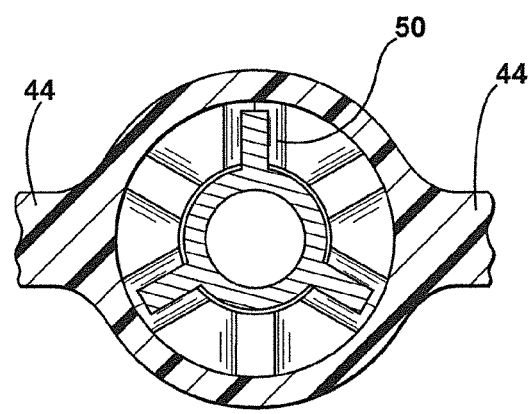

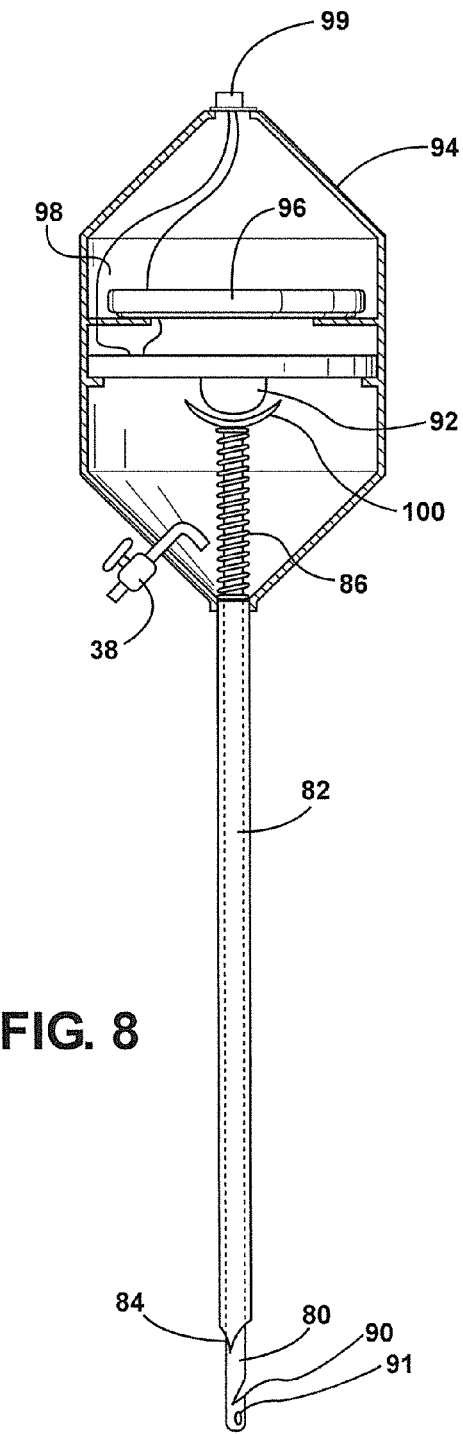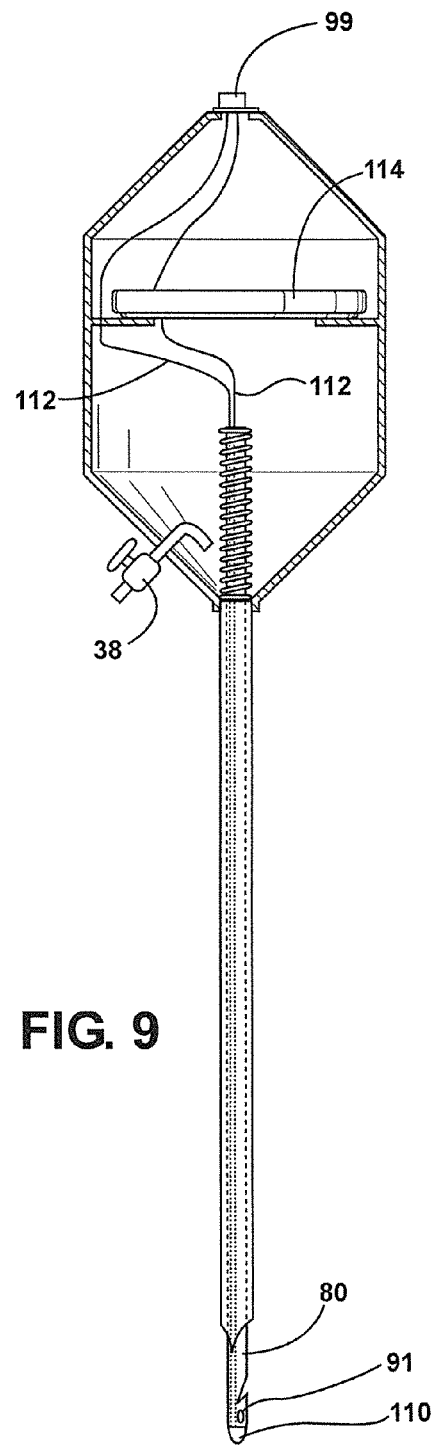

VERESS NEEDLE WITH ILLUMINATED GUIDANCE AND SUTURING CAPABILITY

CROSS-REFERENCE TO RELATED APPLICATIONS

This Application is a Continuation of application Ser. No. 13/965,640 filed Aug. 13, 2013, which is a Continuation in Part of application Ser. No. 12/693,079 filed on Jan. 25, 2010. Application Ser. No. 12/693,079 claims the benefit of U.S. Provisional Application 61/146,974 filed on Jan. 23, 2009.

FIELD OF THE INVENTION

This invention relates to an instrument for use in the practice of laparoscopic surgery and more particularly to such a device which has utility in forming an incision, insufflating the underlying body cavity and suturing the incision at the completion of the surgery.

BACKGROUND OF THE INVENTION

In the practice of minimally invasive laparoscopic surgery it is common to make a small incision through the skin and underlying tissue of the patient adjacent the internal surgical site using a Veress needle. These needles include a tubular outer cannula with a sharpened distal end and an inner hollow cylindrical needle which terminates in a blunt end. A spring assembly urges the needle to a position in which the blunt end of the needle is extended beyond the cutting edge of the cannula. When the instrument is pressed against the skin of the patient the blunt end is resisted by the skin so that the outer cannula moves over the blunt end and forms a small incision in the skin and underlying tissue of the patient. When the pressure on the Veress needle is removed, the needle slides forward, leaving a blunt end within the body of the patient, so that the accidental cutting of underlying organs is avoided.

The Veress needle typically includes means for introducing pressurized gas, usually $CO_2$, into the proximal end of the needle so that the gas is passed on into the laparoscopic incision and inflates the body cavity to allow easy access to the surgical site. A trocar which surrounds the cannula and frames the proximal side of the incision may be left in place after the cannula is withdrawn to provide an instrument port with a seal to prevent the escape of the insufflating gas.

After formation of a first incision and insufflation of the body cavity, a second incision, nearby but spaced apart from the first incision, is formed and typically used for insertion of a remote imaging endoscope to allow the surgeon to visualize the internal surgical site. A third incision allows the insertion of an operating instrument.

When the surgery is completed it is necessary to suture one or more of the laparoscopic incisions. Suturing typically involves an instrument that can carry a suture thread into the body cavity and allow the thread to be pulled outwardly through the incision. At the proximal side of the surgical site two ends of the suture are knotted together to secure the incision.

One problem associated with the use of such Veress needle assemblies is determining when the needle has progressed through the wall of the body cavity and its distal end has emerged within the cavity. Additionally, there is a need to determine the location of significant blood vessels in the cavity wall so that the incision made by the needle, as well as the additional incisions necessary to perform the surgery, can be made without cutting these vessels.

SUMMARY OF THE INVENTION

A first embodiment of the invention, which will subsequently be disclosed in detail, comprises a Veress needle in which the central tube or the rod of the needle supports a grasper at its distal end comprising a pair of pivoted forceps jaws which are normally retained in a closed position by a spring, but may be opened by manual pressure applied to a button at the proximal end of the needle. By opening the jaws, positioning them about a suture line, and depressing the button again, to cause the jaws to clamp on the suture line, a suture may be secured and one end of the suture may be carried externally of the incision by withdrawing the needle.

In another embodiment of the present invention the distal end of the central tube of the Veress needle terminates in a "crochet hook" end facing the proximal end of the needle. The instrument and the suture may be manipulated so that the suture is caught within the hook and drawn out of the incision when the Veress needle is removed. The distal end also has a needle hole through which a suture thread may be passed to carry it into the body cavity.

The preferred embodiment of the invention includes a cam mechanism supported at the proximal end of the instrument which allows the two jaws which make up the hook to be disposed in either an open position, in which the jaws are separated, or a closed position in which the jaws are closed, or closed about a suture. The mechanism includes a button at the proximal end of the instrument which may be depressed to move the hook between its opened and closed positions. With each depression, the hook is moved between its open and closed positions and remains in that state until the button is again depressed, moving the jaws to the other position. This allows a surgeon to manipulate the present instrument with a single hand.

Another aspect of the present invention, illustrated in connection with another embodiment of the invention, comprises an illuminating system for incorporation in a Veress needle assembly which allows the surgeon to visualize the progress of the trocar in forming a laparoscopic incision; aids in the visualization of major blood vessels in the incision area; and, in certain embodiments, provides illumination of the insufflated body cavity to aid in endoscopic visualization of the cavity. These illuminating systems can be incorporated in conventional Veress needle devices as well as the version incorporating the suturing capability.

The illumination system typically employs a bright, small, illumination source such as an LED, although a conventional laser separated from the needle may provide the illumination through an optical fiber. The LED may be located at the proximal end of the Veress needle and cooperate with a hollow tube of a light-conducting plastic such as Lucite, which may form part of the outer cannula, having an appended sharpened end formed of either metal or the tube plastic at its distal end.

In still another embodiment the light source could be located adjacent to the distal end of the cannula and powered by electrical leads passing through the cannula from the proximal end.

The illumination at the distal end of the needle allows the position of the distal end to be visualized by the surgeon through the translucent body tissues. That is, the light from the distal end will pass through the body tissues and allow the surgeon to observe the distal tip of the trocar to determine when it clears the inner wall of the body cavity. It will also aid in identification of major blood vessels which might interfere with the formation of additional incisions required for laparoscopic surgery.

BRIEF DESCRIPTION OF THE DRAWINGS

Other objects, advantages and applications of the present invention will be made apparent by the following detailed description. The description makes reference to the accompany drawings in which:

FIG. 1 is a cross-sectional view through a preferred embodiment of the instrument, with the suture engaging jaws in an open position;

FIG. 1A is a cross-sectional view along line 1A of FIG. 1 illustrating the hook opening and closing mechanism;

FIG. 2 is a cross-sectional view of the device of FIG. 1 with the end hook in a closed position;

FIG. 2A is a cross-sectional view through the device of FIG. 2 along line 2A, again illustrating the hook unlocking and opening mechanism;

FIG. 8 is a side view, partially broken away, of an alternative embodiment of the invention, comprising an LED positioned at the proximal end;

FIG. 9 is a side view, partially broken away, of an embodiment of the invention comprising an LED positioned at the distal end.

DETAILED DESCRIPTION OF THE PREFERRED EMBODIMENT

Figure 3:
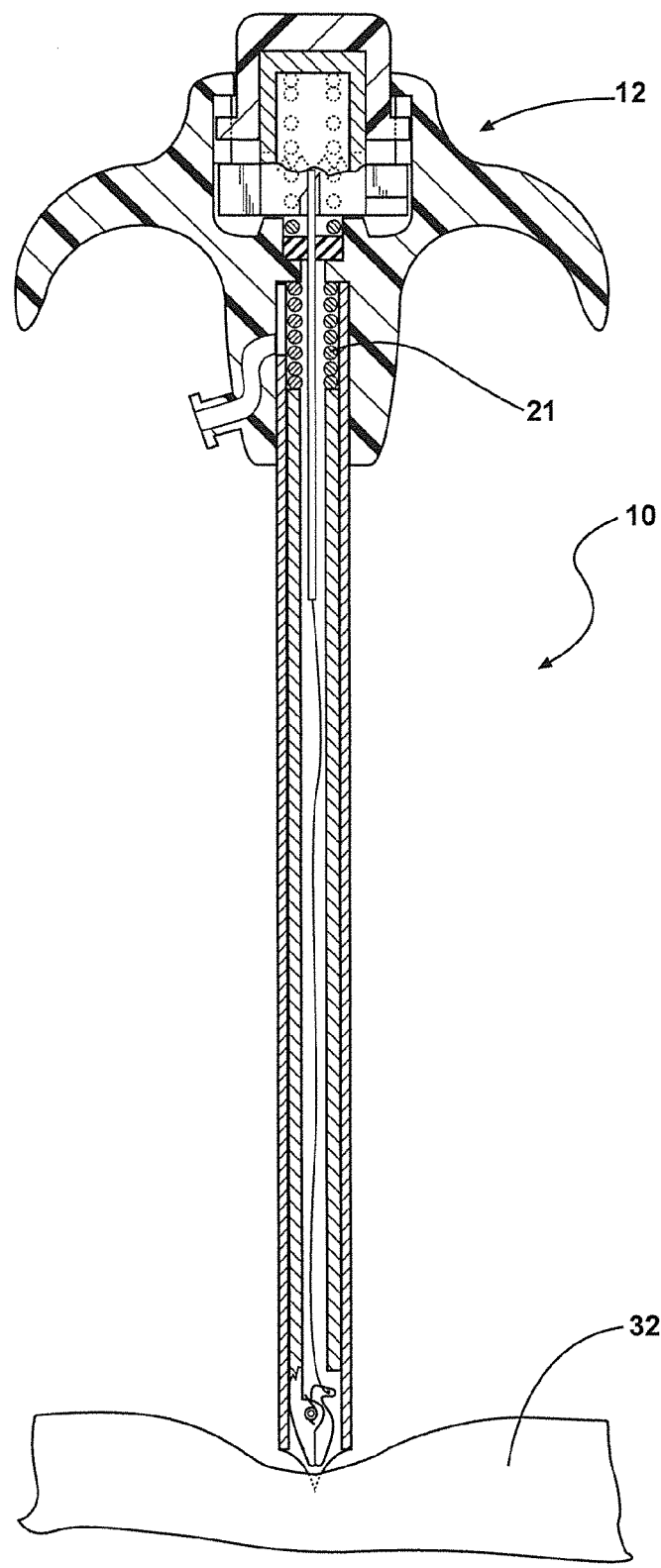
FIG. 3 is a cross-sectional view of the device constituting a preferred embodiment of the invention, illustrating its operation as a Veress needle forming an incision through a body cavity.

A preferred embodiment of the invention, illustrated in FIGS. 1 and 2, acts as a Veress needle to form an incision into a body cavity, as an insufflator to inject gas into the cavity, and as a suture manipulator to close up the incisions made during the endoscopic process.

The instrument, generally indicated at 10, has a handle 12 at the proximal end, which supports one end of the Veress needle, constituting an elongated cannula tube 14 with a sharpened trocar 16 at the distal end. A tubular needle having a diameter complementary to the diameter of the cannula 14 is supported within the cannula.

The distal end of the needle 18 carries one fixed jaw 20 of a suture engaging jaw set. The other jaw member 22 is pivotably connected to the jaw 20 at pivot point 24. A lever arm 26 formed on the jaw 22 connects to one end of a rod 28 which passes through the center of the needle with its proximal end terminating in the handle area 12 at an extension and retraction mechanism which will be subsequently described. When the mechanism extends the rod 28, the jaw 22 moves into a closed position with respect to the jaw 20, as is illustrated in FIG. 2. When the mechanism retracts the rod 28, the jaws are opened as shown in FIG. 1.

Figure 4:
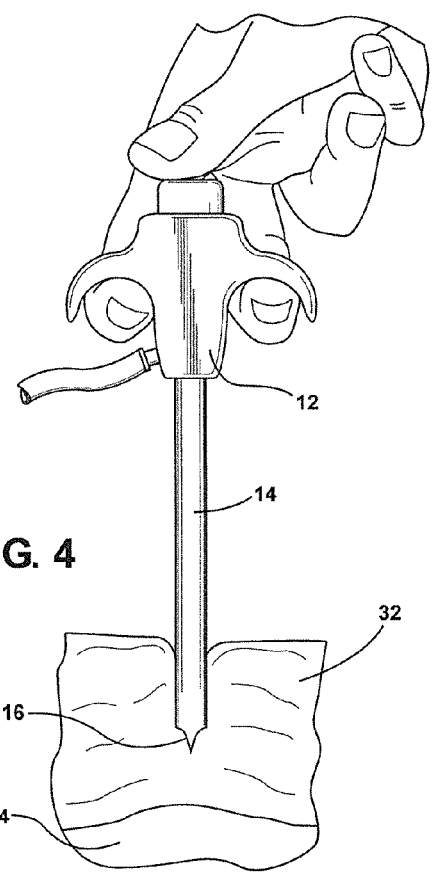
FIG. 4 is a side view of the preferred embodiment of the instrument showing it penetrating wall of a body cavity.
Figure 5:
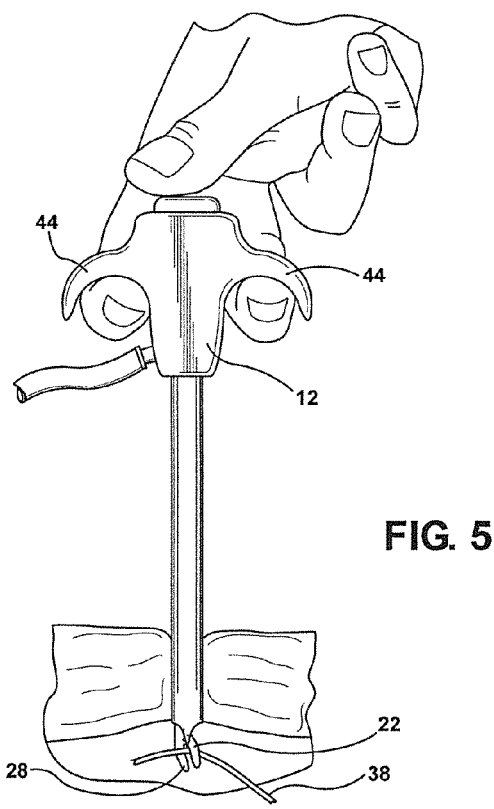
FIG. 5 is a side view of the instrument of the present invention showing it grasping a suture.
Figure 6:
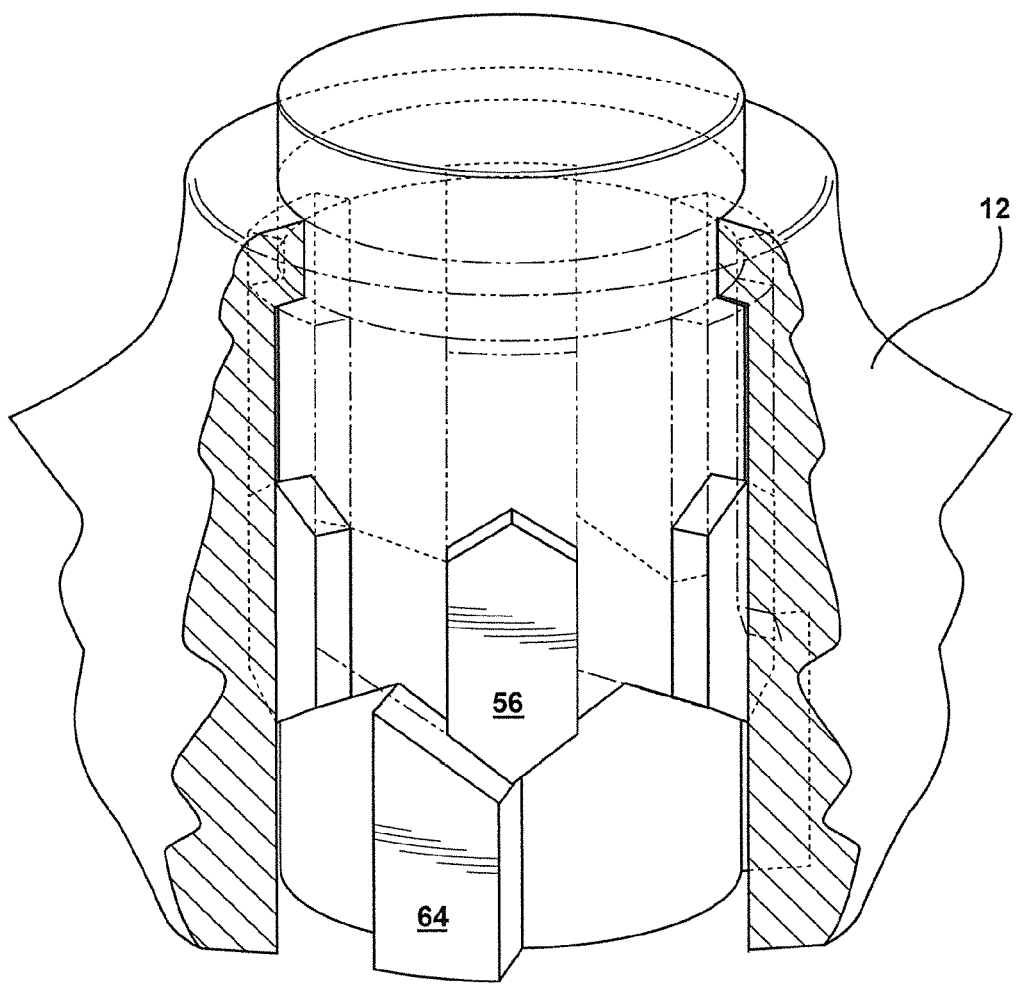
FIG. 6 is a perspective, partially broken-away view of the end hook opening and closing mechanism.
Figure 7:
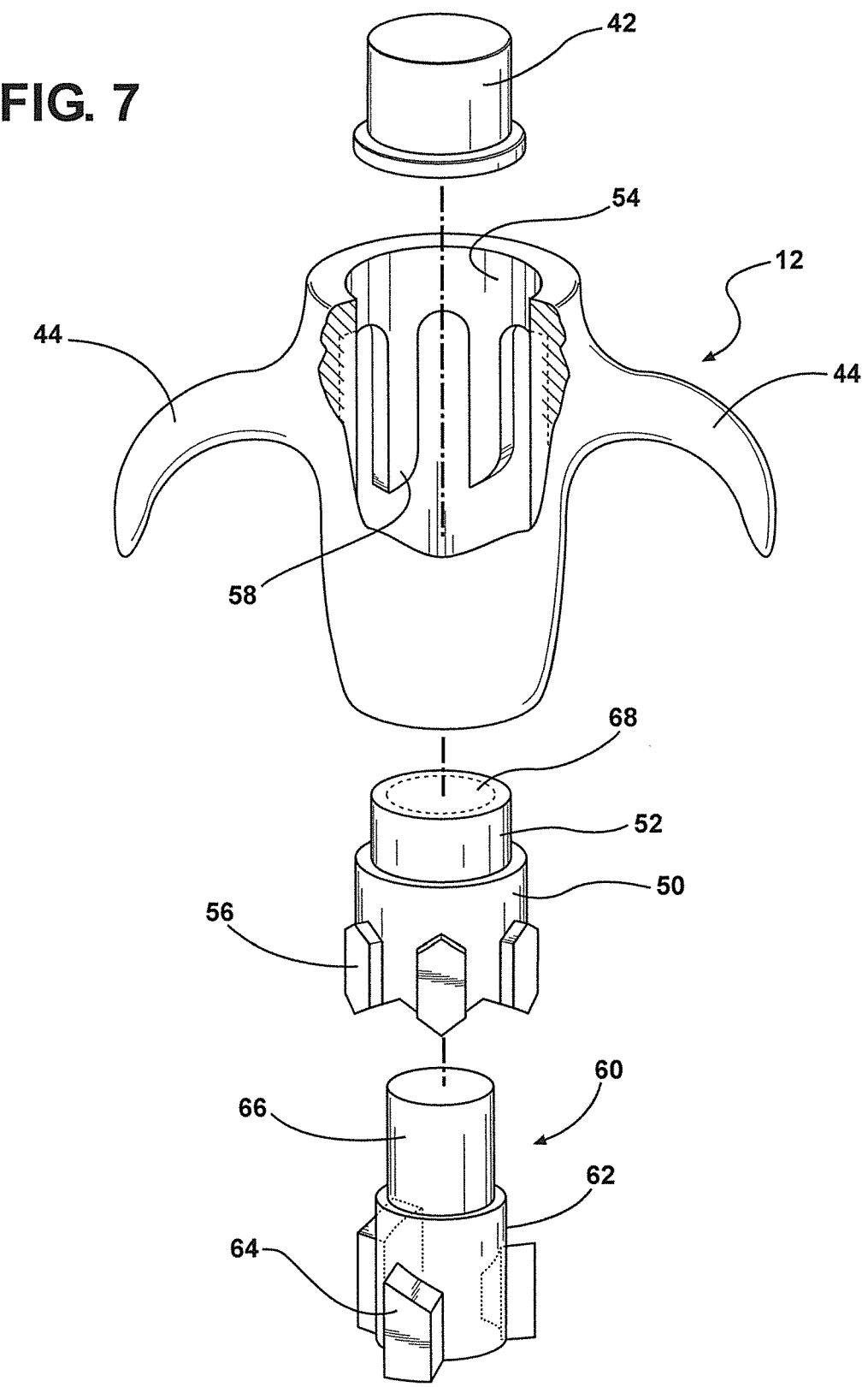
FIG. 7 is an exploded perspective view of the hook-actuating mechanism.

The ends of the jaws 20 and 22 are rounded and blunt. The needle 18 is biased toward the distal end of the cannula 14 by a spring 21 supported in the handle area 12 so that the hook formed by the sections 20 and 22 projects out of the distal end of the cannula. When the instrument 10 is pressed against a wall 32 of a body cavity, in the manner illustrated in FIG. 3 or FIG. 4, and the hook ends are closed, they are forced upwardly against the spring 21 by the contact with the surface of the cavity 32. Thus the sharpened trocar end 16 is forced downwardly beyond the jaws and forms an incision in the body wall 32, in the manner illustrated in FIG. 4.

The body cavity 34 may then be insufflated by gas, preferably $CO_2$, passed through a valve 38 into the interior of the central needle, through the needle, and out the distal end.

The position of the rod 28, which moves the hook between the open and closed positions, is controlled by an extension-retraction mechanism located within the handle 12. A button 42 at the proximal end of the instrument may be depressed by the thumb of the surgeon while two fingers are engaged around the wings 44 of the instrument. The button is normally biased toward extension by a spring 46. The mechanism, which is of the type illustrated in U.S. Pat. No. 4,991,998, the contents of which are hereby incorporated for reference, includes a plunger 50 having an extension 52 at its top end. The plunger moves within a central bore 54 formed in the handle member 12. The opposite end of the plunger 50 includes six laterally extending guides 56 which interact with rails 58 formed on the interior of the cavity 54. The interaction between the guides 56 and the rails 58 restrains the plunger toward longitudinal, non-rotational movement within the handle cavity 54.

A ratchet 60 has a hub 62 from which three guides 64 extend radially. The ratchet 60 has a stem portion 66 which fits within a central void 68 in the plunger 50. Tapered teeth on the upper sides of the three guides 64 engage tapered surfaces on the lower ends of the teeth 58. Thus, when ratchet 60 is inserted into the bore 68 of the plunger 50, the tapered teeth of the plunger and of the ratchet will engage each other and align the parts.

The design of the teeth on the plunger 50, the ratchet 60, and the mechanism on the interior of the interior bore 54 and handle member 12 cause the ratchet 60 to rotate slightly when released from the teeth 58 upon depression of the pushbutton 42 against the upper surface of the plunger 50 and to rotate again when the pushbutton is released so that the teeth 64 engage the teeth 58. The ratchet teeth alternately move from a first position on the teeth 58 into a second position where the teeth 64 slide into the slots between the teeth 58. The ratchet rotates slightly when depressed by the plunger 50 and again on the teeth 58 when the plunger is withdrawn, causing a circular movement that permits the rod 28 to be extended and retracted, thus closing and opening the jaws 20 and 22 and retaining them in that position until the next depression of the pushbutton 42.

Another embodiment of the invention is illustrated in FIG. 8. This version provides a light source at the lower end of a clear polymer rod or tube 80, which extends within a stainless steel hollow tube 82 with a sharp tip 84 on its distal end. A spring 86 biases the interior rod 80 into a position in which its distal end extends outwardly from the tip 84, as illustrated in FIG. 8. Again, when the rounded end of the fiber optic tube 80 is pressed against the body cavity, the tube 80 retracts against the spring and allows the sharp tip to cut into a body cavity and reach an operating site.

Figure 10:
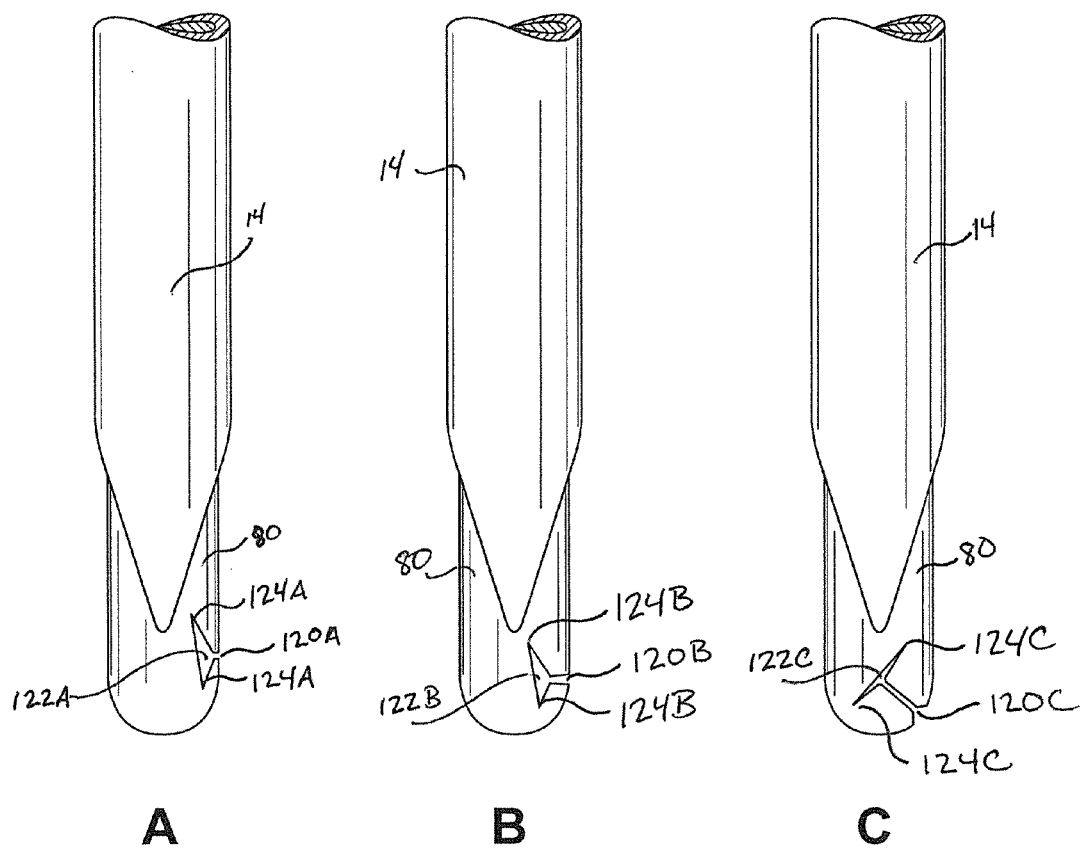
FIGS. 10A, B, and C are side views of the variations of the notch which may be employed with alternative embodiments of the invention.

The tip of the polymer rod 80 is formed with a hook "crochet needle" notch 90, which is adapted to catch a suture and allow it to be withdrawn from the body cavity, as well as a needle hole 91 for carrying a suture into the body cavity. FIGS. 10A, B, and C illustrate variations of the notch which may be employed with alternative embodiments of the invention. Each of the variations includes a narrow passage 120A, 120B, or 120C respectfully formed on the side of rod 80, closely above its distal end. The passages have a width slightly greater than the diameter of the suture. The passages open into triangular sections 122A, B and C connected to the passages at one corner and having acute angles 124 A, B, and C at their other corners. After a suture passes through one of the side openings 120, it may be securely engaged by the rod being manipulated so that the suture is captured in one of the corners 124.

An illumination source 92, preferably taking the form of an LED, is disposed in the proximal end of the instrument within a housing 94.

A battery 96 is also supported in the housing and is connected by leads 98 to the LED 92 through an on-off switch 99. The light from the LED is gathered by a surface 100 and transmitted through the polymer rod 80. The distal end of the rod is polished to produce a light output at that end. The housing 94 is equipped with a gas intake tube and gas valve 38 to allow the insufflation of a body cavity after penetration by the tube 82.

As the surgeon penetrates the body cavity with the device, the polished tip of the rod 80 will provide illumination that is visible through the translucent walls of the cavity, indicating to the surgeon the location of the tip. The surgeon can use that to determine when the device has penetrated into the body cavity and also to identify any major arteries in the cavity wall which should be avoided in the formation of additional laparoscopic openings.

FIG. 9 shows still another embodiment of the invention, generally similar to the device of FIG. 8, with the exception of the fact that the LED 110 is located on the distal tip of the rod 80 and is powered through conductors 112 from a battery 114 supported at the proximal end.

In alternate embodiments of the invention, not shown, a laser of some form other than an LED can be disposed externally of the laparoscopic instrument and the illumination source can be provided by a fiber optic leading from that laser to the desired location of the illumination source.

Having thus disclosed my invention I claim:

1. A device for use in laparoscopic surgery adapted to form an incision in a body cavity and inflate the body cavity with gas passed through the incision, the device comprising:
   a tube having a hollow interior, a tube proximal end and a tube distal end, the tube distal end comprising a tip operable to form the incision;
   an elongated member extending through the tube from the tube proximal end to the tube distal end, the elongated member having a member proximal end and a member distal end, wherein the member distal end has a rounded tip;
   a needle hole formed through the elongated member adjacent the member end operable for carrying a suture through the incision; and
   a notch formed in the elongated member adjacent to the member distal end, the notch having tapered sides with a maximum width at an outer surface of the elongated member and a minimum width at an interior end, wherein the notch is adapted to capture a length of suture thread for withdrawal through the incision.

2. The device according to claim 1, the device further comprising a gas valve for introduction of gas at the tube proximal end for passage through the incision.

3. The device according to claim 1, wherein the elongated member is a polymer rod operable to transmit light received by the member proximal end to the member distal end, and wherein the device further comprises an illumination source operable to emit light on the member proximal end.

4. The device according to claim 3, wherein the illumination source is a light emitting diode.

5. A device for use in laparoscopic surgery adapted to form an incision in a body cavity and inflate the body cavity with gas passed through the incision, the device comprising:
   a tube having a hollow interior, a tube proximal end and a tube distal end, the tube distal end comprising a tip operable to form the incision;
   an elongated member extending through the tube from the tube proximal to the tube distal end and having a member proximal end and a member distal end, wherein the member distal end is rounded and has a notch formed in the elongated member adjacent to the member distal end of the elongated member, the notch having a triangular shape with two acute interior angles and a passage from a third angle to a side of the elongated member adjacent to the distal end, each of the two acute interior angles operable to capture a portion of a suture; and
   an illumination source operable to provide illumination from the member distal end.

6. The device according to claim 5, wherein the elongated member is a polymer rod operable to transmit light received by the illumination source at the member proximal end to the member distal end.

7. The device according to claim 6, wherein the illumination source is a light emitting diode.

* * * * *